US012630032B2

(12) United States Patent
Dabulla et al.

(10) Patent No.: US 12,630,032 B2
(45) Date of Patent: May 19, 2026

(54) CHILLED COMPRESSED AIR ELECTRIC VEHICLE (EV) FAST-CHARGE SYSTEM AND METHOD

(71) Applicant: RSCC Wire & Cable LLC, East Granby, CT (US)

(72) Inventors: Altin Dabulla, Bonita Springs, FL (US); Therese Stevens, Warren, OH (US); Joseph Iamartino, Woodstock, CT (US)

(73) Assignee: RSCC Wire & Cable LLC, East Granby, CT (US)

( * ) Notice: Subject to any disclaimer, the term of this patent is extended or adjusted under 35 U.S.C. 154(b) by 126 days.

(21) Appl. No.: 18/505,413

(22) Filed: Nov. 9, 2023

(65) Prior Publication Data

US 2024/0075832 A1     Mar. 7, 2024

Related U.S. Application Data

(60) Provisional application No. 63/424,080, filed on Nov. 9, 2022.

(51) Int. Cl.
B60L 53/00          (2019.01)
A61K 31/4725      (2006.01)
(Continued)

(52) U.S. Cl.
CPC ........ B60L 53/302 (2019.02); A61K 31/4725 (2013.01); A61K 31/501 (2013.01);
(Continued)

(58) Field of Classification Search
CPC ... B60L 53/302; B60L 53/18; A61K 31/4725; A61K 31/501; A61K 31/5377;
(Continued)

(56) References Cited

U.S. PATENT DOCUMENTS

2016/0221458 A1     8/2016   Lopez et al.
2019/0385765 A1     12/2019  Lyon
(Continued)

FOREIGN PATENT DOCUMENTS

EP          0 823 766 A1     2/1998
EP          3 459 087 A2     3/2019
(Continued)

OTHER PUBLICATIONS

Cheetham et al., "Optimization of a Superconducting Gas-Insulated Transmission Line, " *IEEE Transactions on Dielectrics and Electrical Insulation*, 26(3) (Jun. 2019) (electronic publication).
(Continued)

*Primary Examiner* — Pete T Lee
(74) *Attorney, Agent, or Firm* — Arnold & Porter Kaye Scholer LLP

(57)          ABSTRACT

An air cooling system for an electric vehicle charge cable includes a compressed air supply, at least one filter, at least one dryer and a super cooler subsystem for chilling compressed air from the compressed air supply. A coupling on the charging cable supplies the chilled compressed air to the charging cable. The system is configured to maintain an exterior surface of the charging cable below a predetermined temperature during vehicle charging. The system further includes a routing structure directing the chilled compressed air to flow back to a charging station to maintain the charging cable at a temperature of no more than a predetermined temperature. The system may operate in closed loop mode that is based on geographic climate zone. A method for air cooling an electric vehicle charging cable is also disclosed.

19 Claims, 7 Drawing Sheets

(51) Int. Cl.

| | |
|---|---|
| *A61K 31/501* | (2006.01) |
| *A61K 31/5377* | (2006.01) |
| *A61K 45/06* | (2006.01) |
| *B60L 53/18* | (2019.01) |
| *B60L 53/302* | (2019.01) |
| *C07D 217/06* | (2006.01) |
| *C07D 217/08* | (2006.01) |
| *C07D 217/22* | (2006.01) |
| *C07D 401/12* | (2006.01) |
| *C07D 405/12* | (2006.01) |
| *C07D 413/12* | (2006.01) |
| *H01B 7/42* | (2006.01) |

(52) U.S. Cl.

CPC .......... *A61K 31/5377* (2013.01); *A61K 45/06* (2013.01); *B60L 53/18* (2019.02); *C07D 217/06* (2013.01); *C07D 217/08* (2013.01); *C07D 217/22* (2013.01); *C07D 401/12* (2013.01); *C07D 405/12* (2013.01); *C07D 413/12* (2013.01); *H01B 7/423* (2013.01)

(58) Field of Classification Search

CPC .... A61K 45/06; C07D 217/06; C07D 217/08; C07D 217/22; C07D 401/12; C07D 405/12; C07D 413/12; H01B 7/423

See application file for complete search history.

(56) References Cited

U.S. PATENT DOCUMENTS

| | | | |
|---|---|---|---|
| 2020/0263681 A1 | 8/2020 | Hoff et al. | |
| 2020/0343022 A1 | 10/2020 | Tasiopoulos et al. | |
| 2022/0242260 A1 | 8/2022 | Shoshani et al. | |

FOREIGN PATENT DOCUMENTS

| | | | |
|---|---|---|---|
| EP | 4 067 158 A1 | 10/2022 | |
| EP | 4151450 A1 * | 3/2023 | .............. B60L 53/66 |

| | | | | |
|---|---|---|---|---|
| WO | WO 2015/119791 A1 | 8/2015 | | |
| WO | WO-2018060151 A1 * | 4/2018 | .............. | B60L 53/11 |
| WO | WO 2021/013369 A1 | 1/2021 | | |

OTHER PUBLICATIONS

Davies et al., "Electrical cable tunnel cooling combined with heat recovery, in cities," *Sustainable Cities and Society* 73, pp. 1-11 (Apr. 2019) (Amsterdam, The Netherlands).

Demko, "High-temperature superconducting cable cooling systems for power grid applications—ScienceDirect," *Superconductors in the Power Grid: Materials and Applications* pp. 1-2 (Jan. 2014) (Amsterdam, The Netherlands) (abstract only).

Ding et al., "Thermal Characteristics of Gaseous-Helium-Cooled HTS Cables with Practical Operating Conditions," *IEEE Transactions in Applied Superconductivity* 32(8) pp. 1-7 (Nov. 2022) (electronic publication).

International Search Report dated Mar. 22, 2024 issued in Int'l. Appln. PCT/US2023/079195.

Lopez et al., "Superconducting liquid cryogen insulated power cables for medium voltage applications," *IOP Conference Series: Materials Science and Engineering* 1241(1), pp. 1-8 (May 2022) (electronic publication).

Schweber, "Fluid-Cooled Cable Quadruples EV Charging-Current Capacity," www.electronicdesign.com/markets/automotive/article/21183308/electronic-design-fluid-cooled-cable-quadruples-ev-chargiing-current-capacity (Dec. 2021) (electronic publication).

Shah, "Simulation and Optimization of Cryogenic Heat Sink for Superconducting Power Cable Applications," *Florida State University Libraries* pp. 1-81 (Jun. 2013) (electronic publication).

Stamm et al., "Superconducting Power Cable Design with Hybrid Cryogenic Media - Gaseous Helium for Cooling and Liquid, Nitrogen for Dielectric Insulation," *2020 IEEE Electrical Insulating Conference* pp. 22-26 (Jun. 2020) (electronic publication).

Strong et al., "Module 99: Propane as a refrigerant for use in chillers for air conditioning applications," *CIBSE Journal*, www.cibsejournal.comcpd/modules/2016-09-fgass pp. 1-6 (Sep. 2016) (electronic publication).

Wegner et al., "Combined benefits of cooling with heat recovery for electrical cable tunnels in cities," *Sustainable Cities and Society* 73, pp. 1-11 (Apr. 2019) (Amsterdam, The Netherlands).

* cited by examiner

CHILLED COMPRESSED AIR ELECTRIC VEHICLE (EV) FAST-CHARGE SYSTEM AND METHOD

RELATED APPLICATIONS

This application claims priority to U.S. Provisional Application No. 63/424,080, filed on Nov. 9, 2022, the content of which is incorporated herein by reference in its entirety.

FIELD OF THE INVENTION

The present disclosure relates generally to a charging system for electric vehicles, and more specifically, a chilled compressed air charging system for electric vehicles, and a method for cooling electric vehicle (EV) fast charge cables.

BACKGROUND OF THE INVENTION

Electric vehicles operate on battery power stored in on-board batteries. The batteries are recharged using power supplied from a power grid. There are a number of "levels" of charging. Level 1 charging uses standard, e.g., residential electrical power (120V), which can take many hours to fully charge a vehicle's battery. Level 2 charging uses 220-204V and can often be found in residential, retail, and office charging stations. Level 2 charging can fully charge a vehicle over the course of a workday or night. The most efficient charging is Level 3 charging using "fast chargers" that can charge a vehicle to 80% or more in about 30 minutes and fully charge a vehicle in about 60 minutes.

It will, however, be appreciated that fast chargers operate at high power levels that require cooling the cables between the charging station and the vehicle. Traditional fast charging systems rely on fluid cooling tubes to cool the cables and connectors (the connectors between the cables and the vehicle) due to the heat generated by the power draw. This allows the cables to be "handled" by individuals during charging. Known cooling systems are glycol-based systems, which are complex, high maintenance systems. Further, glycol systems are not necessarily environmentally friendly.

Moreover, as demand for power increases, the diameter of the cable must also increase to accommodate increased power demands. However, cable diameters are limited by current connector designs. Thus, cooling is imperative.

Cooling requirements vary depending on a number of factors. One factor is the current carried by the cable. Another factor is an upper limit of the desired temperature for the cable and connector for user handling. Still another factor is an environmental factor. That is, in cooler climates less cooling may be required, whereas in warmer climates, more cooling may be required. Regardless of the climate factor, a desired temperature for the cable and any associated components is no more than about 140° F. Nevertheless, again, due to the increased power carried by the cables, cooling is required.

U.S. Patent Publication No. 2022/0242260 to Shoshani et al., titled Non-Fluid Cooled Electric Vehicle Fast-Charging Cable, assigned to the assignee of the present application, discloses embodiments of cables that can be used in fast charging system and function without the use of a liquid cooling fluid.

Accordingly, there is a need for a system for fast-charging EVs that uses a gaseous cooling medium. Desirably, such a system uses forced air as the cooling medium. More desirably still, such a system is flexible and can include multiples of each component to accommodate differing and various environmental factors and achieve predetermined cable and connector exterior temperatures for ease of handling.

SUMMARY OF THE INVENTION

Aspects of this disclosure relate to an air cooling system for an electric vehicle charge cable includes a compressed air supply, at least one filter, at least one dryer, and a super cooler subsystem for chilling compressed air from the compressed air supply. A coupling on the charging cable supplies the chilled compressed air to the charging cable. The system is configured to maintain an exterior surface of the charging cable below a predetermined temperature during vehicle charging. For example, the system is configured to reduces the surface temperature of an EV fast charge cable and associated components to less than about 140° F. by forcing chilled and dried air through cooling channels in the fast charge cable and a connector handle for the charge cable. In various embodiments, to achieve this, dried and compressed air at a desired flow rate is chilled and supplied to cooling channels in the charging cable. In various embodiments, the system further includes a routing structure directing the chilled compressed air to flow back to a charging station to maintain the charging cable at a temperature of no more than a predetermined temperature. In some embodiments, the system may be configured to operate in a closed loop mode based on geographic climate zone. A method for air cooling an electric vehicle charging cable is also disclosed herein.

In various embodiments, the super cooler subsystem includes a refrigerant cycle. The air chilling system can further include a heat exchanger. In such an embodiment, the heat exchanger includes a refrigerant side and an air side. The heat exchanger can be within the super cooler subsystem.

In various embodiments, a filter of the air cooling system may comprise a hydrocarbon filter and the dryer may comprise a desiccant dryer. The system may include multiple filters and/or dryers.

In some embodiments, the air chilled electric vehicle charging cable and system may include first and second electric vehicle charging cable portions. Each cable portion may include an insulated conductor carried in a jacket. The jacket may include a wall having an inner surface and defining a cooling channel extending longitudinally along the charging cable, between the jacket and the insulated conductor.

In various embodiments, the system may include a compressed air supply, one or more filters, one or more dryers, and a super cooler subsystem. The system further includes a coupling on each charging cable portion for supplying chilled air to the charging cable portions' air channels. In some embodiments, the charging cable cooling channel can be a series of cooling channels. In some embodiments, the series of cooling channels can be formed by a series of inwardly extending fingers extending inwardly from the inner surface. The fingers may be configured to space the insulator from the jacket wall. In some embodiments, the inwardly extending fingers are spaced from one another to define air channels between the fingers that extend longitudinally along the cable.

In some embodiments, the charging cable can further include a connector handle, and the first and second charging cable portions terminate at the connector handle. Exhaust vents can be formed in the connector handle for discharge of the chilled air from the charging cable portions' air channels. The exhaust vents can be stationary or movable.

In yet another aspect, a method is disclosed for air cooling an electric vehicle charging cable. Such a cable has first and second electric vehicle charging cable portions, each portion including an insulated conductor carried in a jacket, the jacket having a wall having an inner surface and defining a cooling channel extending longitudinally along the charging cable, between the jacket and the insulated conductor.

The method includes compressing air to a predetermined pressure, filtering the compressed air, drying the compressed and filtered air, and chilling the compressed, filtered and dried air in a super cooler, the super cooler having a refrigeration cycle. The compressed, filtered, dried and chilled air is introduced into the cable cooling channel. The air is discharged from the cooling channel at a connector handle. In methods, the air is compressed to a pressure such that the air exiting the exhaust or vent is at a noise level of no more than about −65 db.

The method further includes directing the compressed, filtered, dried and chilled air at a routing structure of a connector handle to flow back to a charging station to maintain the charging cable at a temperature of no more than a predetermined temperature. The method further includes discharging the air away from the vehicle depending on ingress rating requirements of a connector handle.

These and other objects, features, and characteristics of the invention disclosed herein will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The present invention is illustrated by way of example and not limited in the accompanying figures in which like reference numerals indicate similar elements and in which.

These drawings are provided for purposes of illustration only and merely depict typical or example embodiments. These drawings are provided to facilitate the reader's understanding and shall not be considered limiting of the breadth, scope, or applicability of the disclosure. For clarity and ease of illustration, these drawings are not necessarily drawn to scale.

DETAILED DESCRIPTION

In the following description of various examples of the invention, reference is made to the accompanying drawings, which form a part hereof, and in which are shown by way of illustration various example structures, systems, and steps in which aspects of the invention may be practiced. These aspects are indicative, however, of but a few of the various ways in which the principles of the invention may be employed and the present invention is intended to include all such aspects and their equivalents. It is to be understood that other specific arrangements of parts, structures, example devices, systems, and steps may be utilized, and structural and functional modifications may be made without departing from the scope of the present invention. Also, to the extent the terms "top," "bottom," "front," "back," "side," and the like are used in this specification to describe various example features and elements of the invention, these terms are used herein as a matter of convenience, e.g., based on the example orientations shown in the figures. Nothing in this specification should be construed as requiring a specific three-dimensional orientation of structures in order to fall within the scope of this invention.

Embodiments of an air chilling system reduce the surface temperature of an EV fast charge cable and associated components to less than about 140° F. by forcing chilled and dried air through cooling channels in the fast charge cable and a connector handle for the charge cable. In systems, dried and compressed air at a desired flow rate is chilled and supplied to cooling channels in the charging cable. In various embodiments, chilling of the air will be on-demand, that is, the compressed air is chilled as cooling of the cable and components is needed (e.g. during charging). The specific flow rates and cooling loads will vary depending on the local climate and seasonal temperature variations. The HVAC industry generally recognizes seven defined zones for climate control. As such, the specific components and numbers of each component needed to achieve the desired cooling may vary depending on the location of and environmental conditions at the EV charging system.

Figure 1:
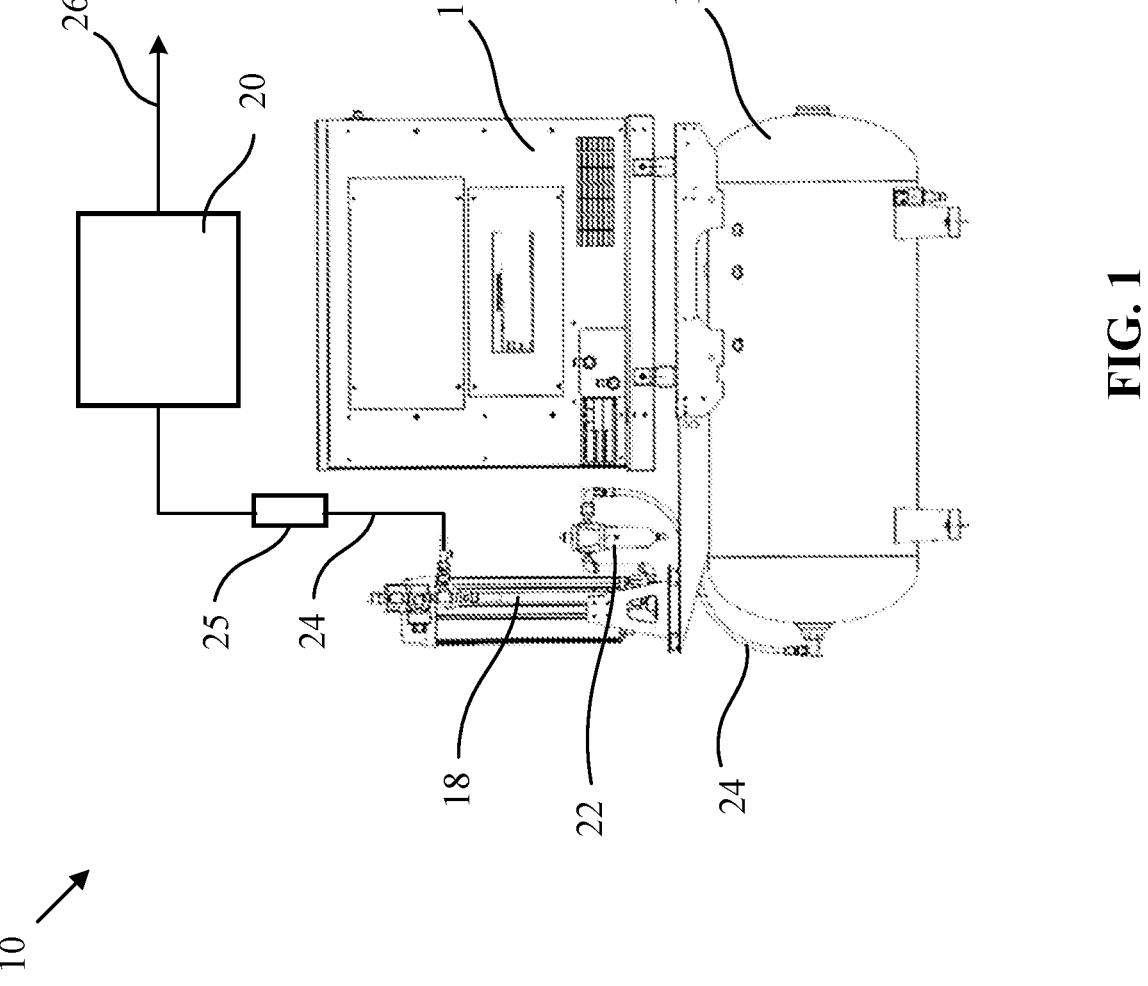
FIG. 1 is a schematic illustration of an air supply system for an EV fast-charge system according to one or more aspects described herein.
Figure 2:
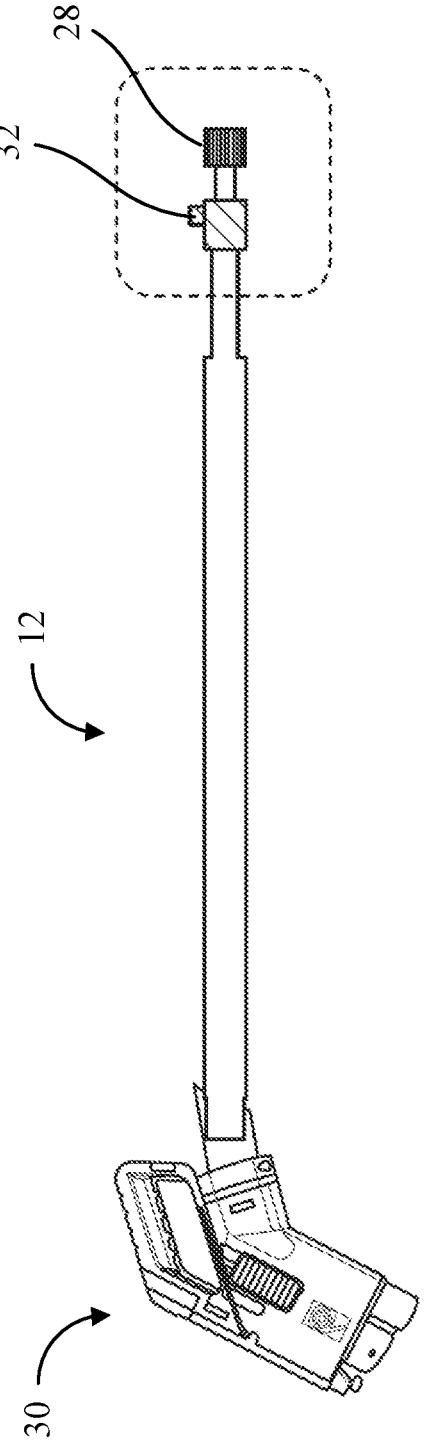
FIG. 2 depicts a side view of an example fast-charge cable and connector handle for use with the components of the air supply system, according to one or more aspects described herein.
Figure 4B:
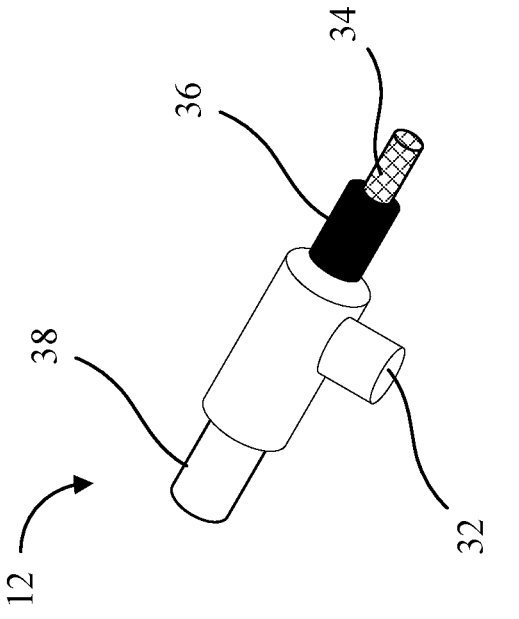
FIGS. 4A-B depict various views of an example fast-charge cable and air coupling, according to one or more aspects described herein.

FIG. 1 is a schematic illustration of an example embodiment of an air supply system 10 for an EV fast-charge system cable, according to one or more aspects described herein. For example, air supply system 10 may be configured for use with fast-charge cable 12 depicted and described further herein. In various embodiments, air supply system 10 may include an air compressor 14 or other supply of compressed air, a compressed air holding tank 16, one or more air dryers 18 (e.g., such as a desiccant dryer), and/or a super cooler 20 comprising a refrigerant based cooling or chilling system for the compressed air. In some embodiments, air supply system 10 may include one or more filters 22, lines/conduits 24 between the system components, and/or one or more other components. In various embodiments, compressed air from the air supply system 10 may tie into a fast-charge cable via a compressed air supply line 26, which may tie-in downstream of the cable attachment or lug 28 (e.g., as depicted in FIGS. 2 and 4B) to a power supply (not shown).

In various embodiments, the compressor 14 may comprise an oil-free compressor, such as an oil-free scroll compressor. Such a compressor may not expel oil into the air system. The holding tank 16 can be of any appropriate type that is manufactured for the storage of a pressurized gas, such as pressurized (compressed) air. In an example embodiment, the holding tank 16 may have a capacity of about 120 gallons, but an appropriately sized tank will be appreciated by those skilled in the art. In some embodiments, a 120 gallon tank may reduce the start/stop cycling of compressor 14 to about 5 to 6 cycles per hour. In some embodiments, the storage tank 16 may also provide additional holding time for the compressed air to cool following the compression cycle (compression tends to increase the temperature of the gas exiting the compressor 14).

In various embodiments, air supply system 10 includes one or more filters 22. In various embodiments, a first filter downstream of compressor 14 and holding tank 16 may comprise a hydrocarbon filter 22. Hydrocarbon filter 22 may be configured to remove asphalt, diesel, gasoline, and other hydrocarbon fumes that may be in the compressed air. In various embodiments, air supply system 10 may also include a desiccant dryer 18 downstream of the holding tank 16, as well as a particulate filter 25 downstream of the desiccant dryer 18 to remove particulates that may be present in the compressed air stream. In some embodiments, air supply system 10 may include an after-chiller (not shown) upstream of the super cooler 20 (e.g., between the desiccant dryer 18 or particulate filter 25 and the super cooler 20) to further dry the air prior to the super cooler 20.

In various embodiments, the desiccant dryer 18 is located downstream of the hydrocarbon filter 22 and removes moisture from the compressed air. Such a dryer 18 is most useful in cold and/or moist or humid environments. In various embodiments, super cooler 20, which may comprise a refrigerant based cooling or chilling system, further reduces the temperature of the compressed air prior to discharge to the air supply line 26. The size and capacity of the super cooler 20 may depend on local environmental factors, such as local temperature and temperature ranges, temperature and humidity of the inlet air, and the like.

Figure 4A:
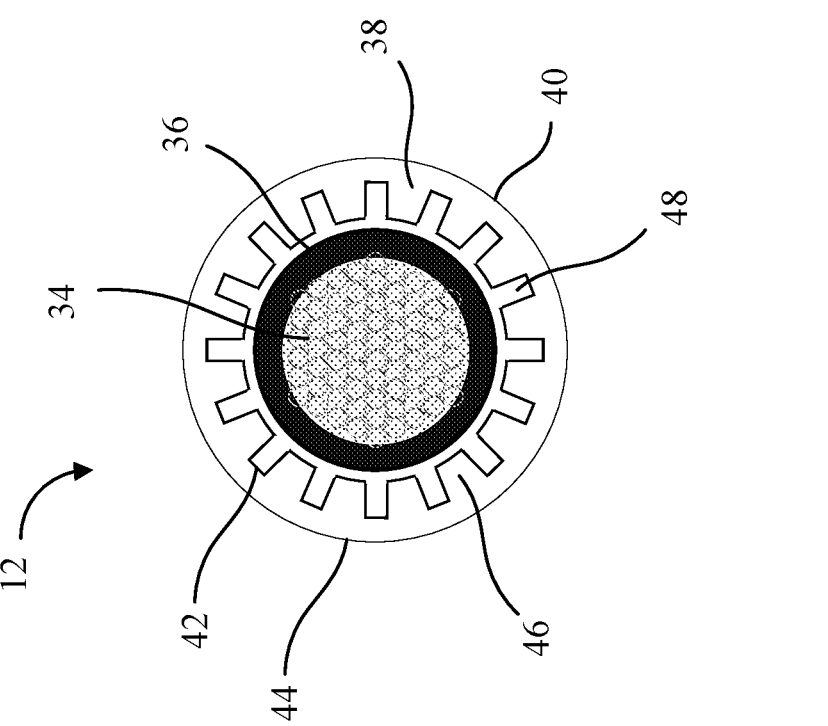

FIG. 2 illustrates a portion of a representative fast-charge cable 12 and connector handle 30 for use with the components of air supply system 10, according to one or more aspects described herein. As depicted in FIG. 2, an air coupling 32 and power lug 28 may be provided to connect fast-charge cable 12 to air supply system 10. Referring briefly to FIGS. 4A-B, various views of fast-charge cable 12 and air coupling 32 are depicted, according to one or more aspects described herein. For example, FIG. 4A depicts a cross-sectional view of fast-charge cable 12, and FIG. 4B depicts a perspective view of air coupling 32, according to one or more aspects described herein. In various embodiments, cable 12 may include a multi-strand conductor 34, an insulator 36 surrounding the conductor 34, and a jacket 38 surrounding the insulator 36. In various embodiments, the cable 12 may include air channels 48 that run parallel to the conductors to move the chilled and compressed air longitudinally through the cable 12 from the coupling 32 to the connector handle 30.

Figure 6:
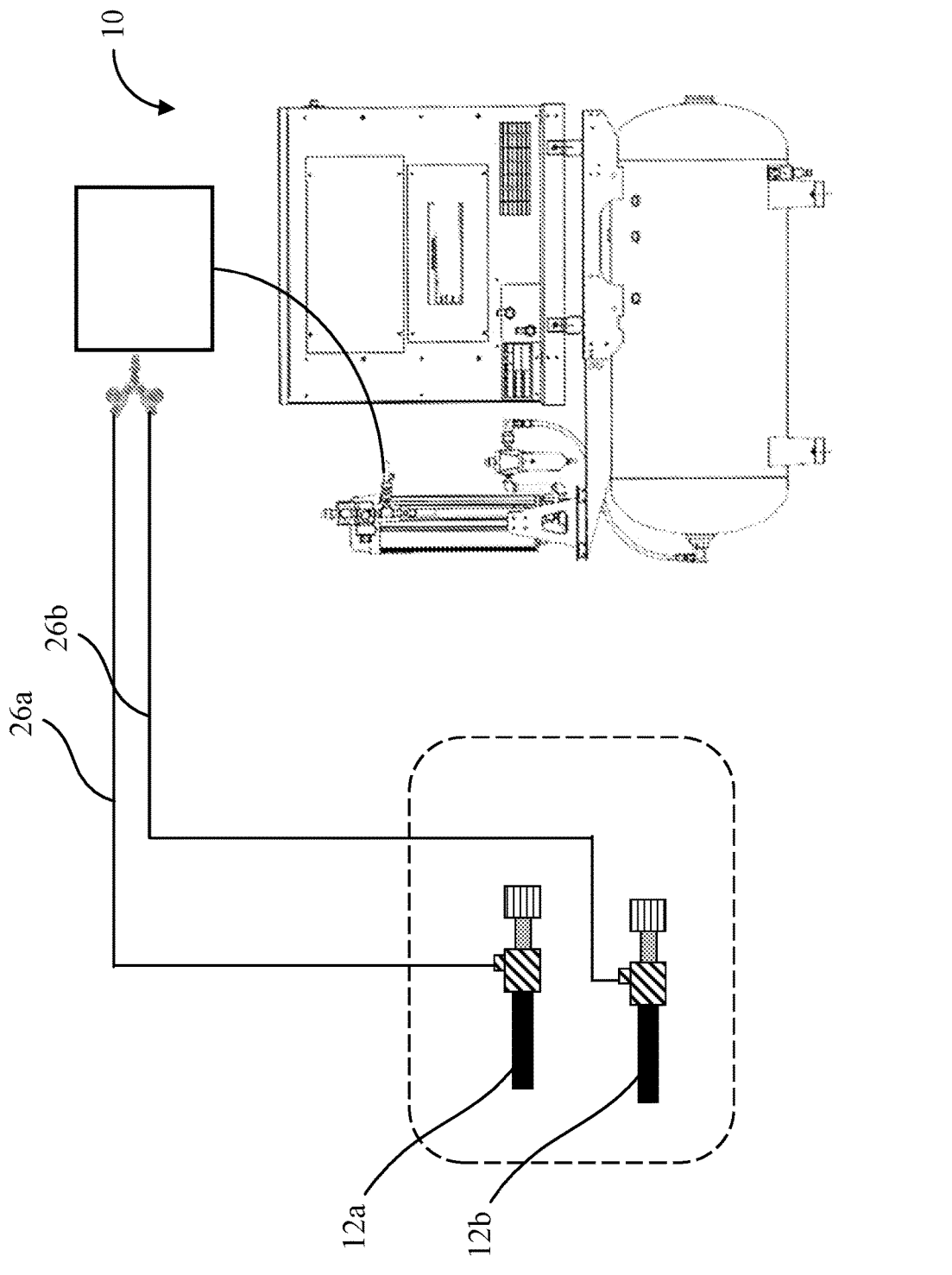
FIG. 6 is a schematic illustration of an air supply system similar to FIG. 1 having two air supply lines from the supply system to two fast-charge cables, according to one or more aspects described herein.

In some embodiments, the jacket 38 of cable 12 may include a wall 40 having inner and outer surfaces 42, 44 and a series of inwardly extending fingers 46 that extend inwardly from inner surface 42 to the insulator 36, and space the insulator 36 from the jacket 38. In various embodiments, the fingers 46 are spaced from one another to define air channels 48 between the fingers 46 that extend longitudinally along the cable. It will be understood that the fast charge cable 12 may require two conductors 34 (and thus the two portions of cable 12) and two supply lines 26 from the cooling system 10. For example, FIG. 6 provides a schematic illustration of one example of a fast charge cable 12 that includes the two cable portions 12a and 12b (i.e., two jacketed (38) insulated power conductors 34) and two air supply lines 26, according to one or more aspects described herein. Examples of such a cable are also described in detail in the aforementioned U.S. Patent Publication No. 2022/0242260 to Shoshani et al. Other configurations of cables 12 that include air channels will be appreciated by those skilled in the art and are within the scope and spirit of the present disclosure.

The example air coupling 32 depicted in FIG. 4B shows a juncture in the cable jacket 38 for tying the air supply line 26 to the fast-charge cable portion 12a. As shown, the insulated conductor 34 may extend longitudinally through the jacket 38, and the juncture or tie-in of the air supply line 26 to the jacket 38 may bring the air supply line 26 into the jacket 38 at an angle to a portion of cable 12. The exposed portion of the conductor 34 shown in FIG. 4B may be connected to power lug 28 within the charger (not shown). The air coupling 32 may be configured such that, as the cable 12 is manipulated (i.e., taken from a receptacle at the charger, plugged into the vehicle and returned to the charger receptacle), the coupling 32 does not kink the jacket 38 or cable 12. In this manner, the system may cause air to flow equally or substantially equally through the air channels 48 in the jacket 38. In various embodiments, the coupling 32 may be sealed to the cable 12 by seals, epoxy or the like.

Figure 3:
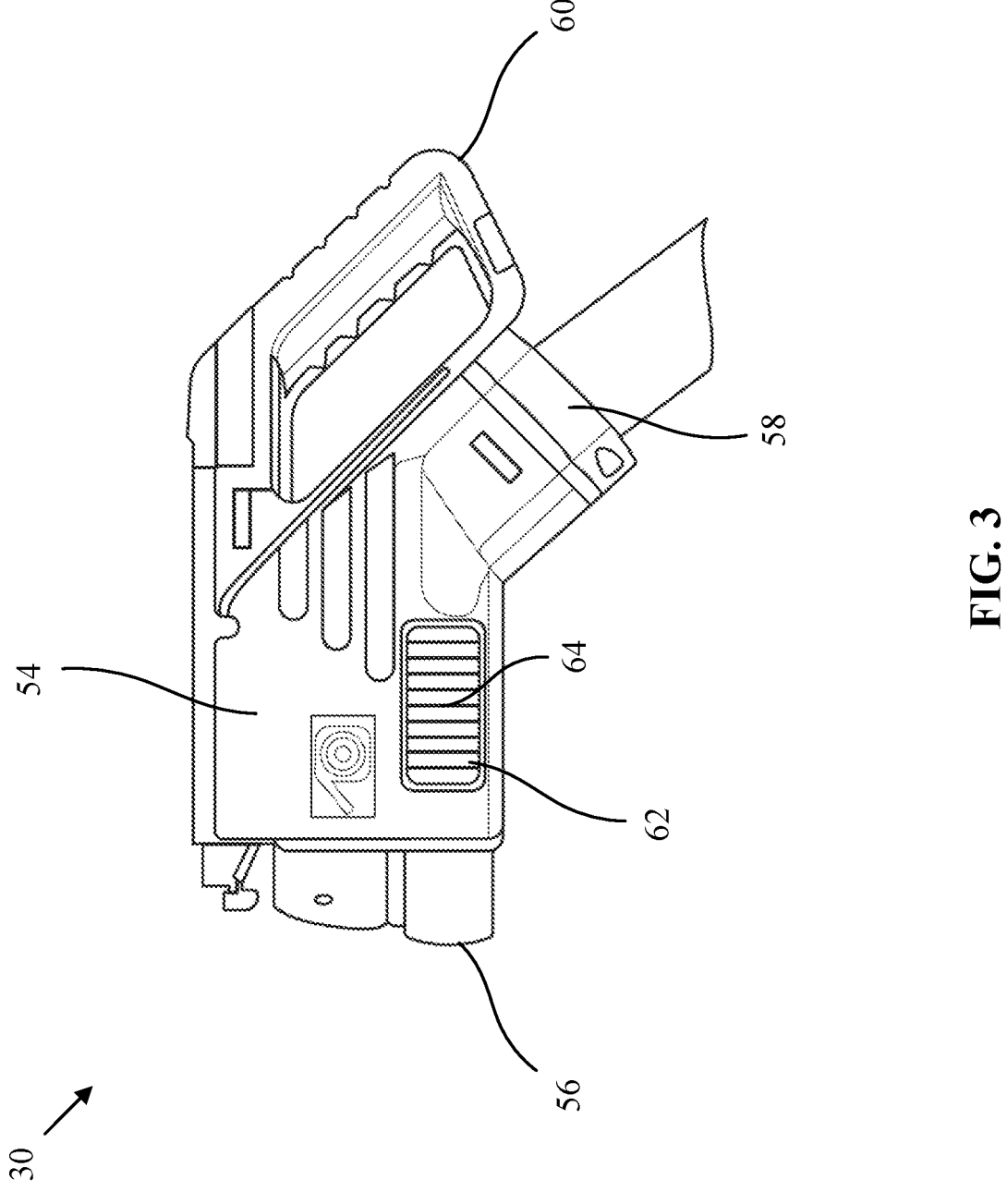
FIG. 3 depicts a side view of an example connector handle for a fast-charge cable, according to one or more aspects described herein.

In various embodiments, the connector handle 30, which is depicted in FIGS. 2 and 3, provides the connection of the cable 12 to the vehicle and also provides an outlet for the chilled and compressed air. The configuration of the connector handle 30 may be such that the compressed and chilled air travels through the handle 30 and is discharged from the handle 30 to maintain the handle 30 at a temperature of no more than about 140° F. In various embodiments, the handle 30 may comprise a body 54, a connector portion 56 for connecting to an electric vehicle, a cable receiver 58, a hand grip portion 60, an air exhaust 62, and/or one or more other components. In various embodiments, fast-charge cable 12 may enter the handle 30 at the cable receiver 58, and the conductors 34 terminate at connector portion 56 for connecting to the electric vehicle. The cable jacket 38 may be open to the interior of the handle 30 at the cable receiver 58 and provide a path for the chilled air from the cable 12 through the handle 30. The air may exhaust from the handle 30 at air exhaust 62. In various embodiments, the air exhaust 62 may comprise a vented opening having a series of spaced slats 64 (e.g., shark gills) for exhaust of the air through the spaces between the slats 64. The slats 64 may be stationary or movable. To pass immersion and dust ingress tests, it may be necessary to close the vent(s) 62 (or slats 64) when the recharging system is not running. In addition it may also be necessary to use gaskets, sealants, and/or the like to secure/close off other portions of the interior of handle 30.

Figure 5:
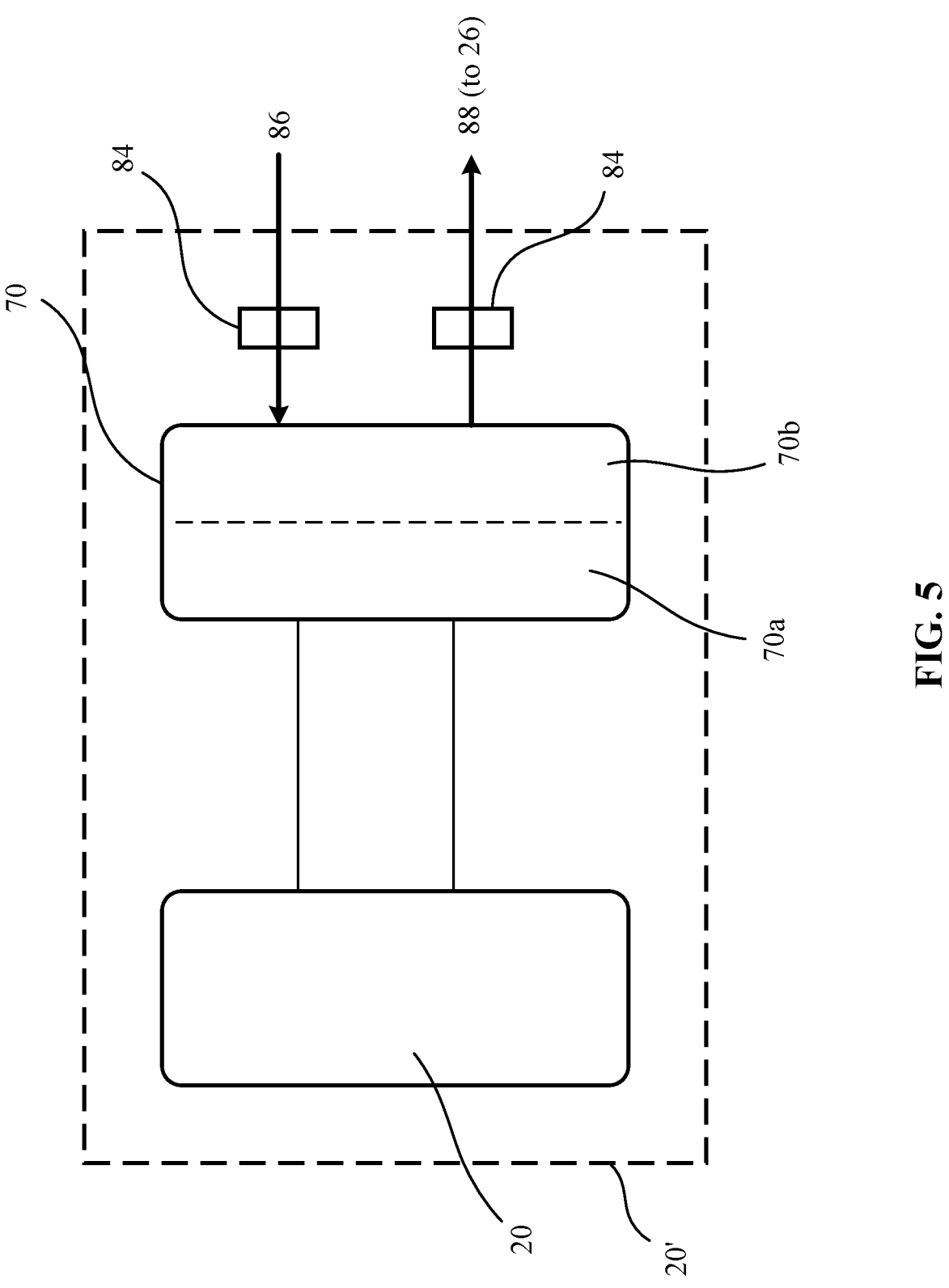
FIG. 5 is a schematic illustration of a super cooler subsystem for the air supply system, according to one or more aspects described herein.

FIG. 5 is a schematic illustration of a super cooler subsystem 20' for air supply system 10, according to one or more aspects described herein. The super cooler 20 can take many forms, as will be appreciated by those skilled in the art. In various embodiments, super cooler 20 is configured to cool or chill the dry inlet air. For example, in a particular environment or HVAC zone, the super cooler 20 may be configured to chill the dry air from about 45° C. (113° F.) to about 10° C. (50° F.). One suitable super cooler 20 may be a refrigerant based cooling or chilling system to further reduce the temperature of the compressed air prior to discharge to the air supply line 26. In various embodiments, air supply system 10 may include a heat exchanger 70 having a refrigerant side or subsystem 70*b* through which the refrigerant circulates, and a chilled air side 70*a*. In some embodiments, the heat exchanger 70 may be incorporated into the super cooler 20 (forming a super cooler subsystem 20'). To maintain desired outlet chilled air temperatures, temperature sensors 84 may be located at the inlet and outlet air streams 86, 88, respectively of the heat exchanger 70 (at the air side 70*b* of the heat exchanger 70).

When implemented, air supply system 10 may facilitate a method for air cooling a fast charge EV cable (such as cable 12 depicted and described herein). In various implementations, the method may include compressing air in a compressor 14 to a pressure such that the system will operate with an audio noise level of no more than about −65 db at the charge handle exhaust or vent 62. The compressed air can be stored in, for example, a holding tank 16. The compressed air is then filtered in a filter 22. A suitable filter 22 includes, for example, at least one hydrocarbon filter to remove asphalt, diesel, gasoline, and other hydrocarbon fumes that may be present in the compressed air.

The filtered air is then dried in, for example, a desiccant dryer 18 to remove moisture from the compressed air. A desiccant dryer 18 may be the most beneficial in cold and/or moist or humid environments. The filtered and dried air may then be filtered in a particulate filter 25.

The filtered and dried air can then be cooled in a super cooler 20. One suitable super cooler 20 is a refrigerant based cooling or chilling system to further reduce the temperature of the compressed air prior to discharge to the air supply line 26.

Figure 7:
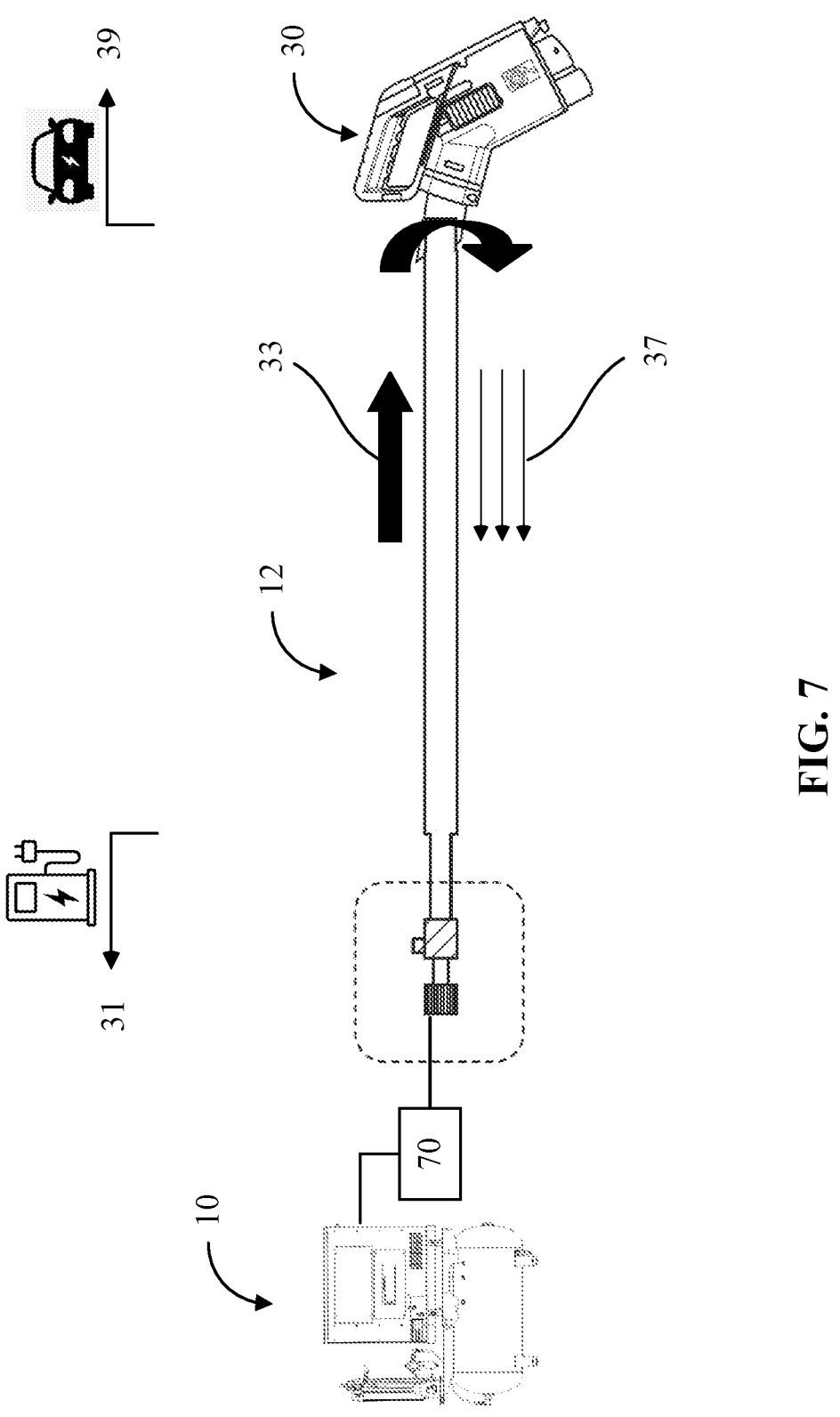
FIG. 7 is a schematic illustration of the air supply system described herein when used with an alternative embodiment of the fast-charge cable and connector handle, according to one or more aspects described herein.

FIG. 7 illustrates an alternative embodiment of fast-charge cable 12 and connector handle 30, according to one or more aspects described herein. In various embodiments, heated air may be vented at a vehicle end 39 or away from the vehicle depending on ingress (e.g., moisture and/or dust) rating requirements of the EV charger. For example, in some embodiments, handle 30 may be configured to provide connection of the cable 12 to the vehicle and further comprises a routing structure (not shown) within the body 54 of handle 30 for the chilled and compressed air. The configuration of the connector handle is such that the compressed and chilled air travels and is directed (i.e., re-routed) at the routing structure of the handle, and flows back to charging station to maintain the handle at a temperature at or below a pre-determined temperature. For example, as depicted in FIG. 7, compressed and chilled air 33 travels from a charging station end 31 of cable 12 via one or more air channels 48 (as depicted in FIG. 4A) and is re-directed (or re-routed) at the routing structure of the handle 30 at a vehicle end 39 of cable 12. Heated air 37 may flow back to the charging station end 31 to maintain the handle at a temperature of no more than a pre-determined temperature, e.g., about 140° F.

In various embodiments, compressed and chilled air 33 may travel from a charging station end 31 via one or more air channels 48 located around insulation of insulated conductor equally spaced apart circumferentially, and heated air 37 may flow back to the charging station end 31 remaining air channels 48 located around insulation of insulated conductor equally spaced apart circumferentially. In some embodiments, compressed and chilled air 33 may travel from a charging station end 31 via one or more air channels 48 located around insulation of insulated conductor equally spaced apart circumferentially, and heated air 37 may flow back to the charging station end 31 additional air channels located within the cable. It is to be understood, however, that the one or more air channels 48 may be used with any appropriate configuration without departing from the scope of the invention described herein.

The air returned back through the cable may be vented at the charging station end 31, e.g., rear side of the air supply system 10 adjacent to connections for DC power and/or charger itself. In such embodiments, heated air may vent away from the vehicle that is plugged in and being charged. Accordingly, heated air may be vented at a vehicle end 39 or away from the vehicle end depending on ingress rating requirements of the EV charger.

In some embodiments, air supply system 10 may be further connected to one or more of air pulling devices, e.g., an extraction fan and/or a vacuum pump, to pull the heated air back to the air supply system 10 and further enhance the cooling efficiency.

In various embodiments, air supply system 10 may be configured to operate at an open or closed loop modes for heat evacuation depending on geographical conditions. In some embodiments, air supply system 10 may be operated at closed loop modes based on geographic climate zones used for heating/cooling. For example, air supply system 10 located in a tropical climate zone may be operated at closed loop modes optimized for high temperatures than air supply system 10 located in a polar climate zone. Similarly, air supply system 10 located in a tropical climate zone may be operated at closed loop modes optimized for high precipitation than air supply system 10 located in a dry climate zone. In some embodiments, a closed loop configuration may further use a heat exchanger 70 (as disclosed in FIG. 5) to actively pull the heat out of cable 12.

In some embodiments, heat from the evacuation process may be utilized to keep air supply system 10 in a walk-in-closet (WIC)/outside rated shed at an optimum temperature in case of low temperatures (during cold season). Various types of seasonal use of heated air will be appreciated, particularly, in northern hemisphere regions.

In other embodiments, WIC may include a cooling system to ensure optimal shed's temperature in case of high temperatures (during heat season). In particular embodiments, one or more of compressed air tanks may be installed underground to take advantage of low temperature, for example, temperature of about 55° F. below ground, as well as for improved temperature consistency.

When implemented, the method described herein may further include providing the filtered and chilled air to an EV fast charge cable 12, which cable has at least a pair of insulated conductors 34, each carried in a jacket 38. One or more air channels 48 are formed between the jacket 38 and the insulated conductor 34 and the method includes forcing the chilled and dried air through the air channels 48 to cool the charge cable 12 and connector handle 30. In various implementations, the air exits the cable 12 at the connector handle 30. The handle 30 can include vents 62 through which the air exits.

It will be appreciated that the present system 10 uses cooled or chilled compressed air to effectively cool fast-charge EV charging systems. Such a system is flexible and can include multiples of each component to accommodate differing and various environmental factors and achieve predetermined cable and connector exterior temperatures for ease of handling. In such systems, dried and compressed air at a desired flow rate is chilled or cooled and supplied to cooling channels in the charging cable on-demand. That is, the compressed air is chilled as cooling of the cable and components is needed (e.g. during charging).

Those skilled in the art will appreciate the advantages of a fast-charge EV cable that does not require cooling coils, thus eliminating the cooling fluid, fluid connections, and potential leakage. Although certain materials for the insulation, binder, thermal blanket, and jacket are disclosed, those skilled in the art will recognize the other suitable materials that may be used for the fast-charge EV cable, which other materials are within the scope and spirit of the present disclosure. It will also be recognized that the various materials and layers in any disclosed embodiment may be used with others of the embodiments and that all such embodiments and variations thereof are within the scope and spirit of the present disclosure.

It is to be understood that the invention is not limited in its application to the details of construction and the arrangement of the components set forth herein. The invention is capable of other embodiments and of being practiced or being carried out in various ways. Variations and modifications of the foregoing are within the scope of the present invention. It should be understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

While the preferred embodiments of the invention have been shown and described, it will be apparent to those skilled in the art that changes and modifications may be made therein without departing from the spirit of the invention, the scope of which is defined by this description.

Reference in this specification to "one implementation", "an implementation", "some implementations", "various implementations", "certain implementations", "other implementations", "one series of implementations", or the like means that a particular feature, design, structure, or characteristic described in connection with the implementation is included in at least one implementation of the disclosure. The appearances of, for example, the phrase "in one implementation" or "in an implementation" in various places in the specification are not necessarily all referring to the same implementation, nor are separate or alternative implementations mutually exclusive of other implementations. Moreover, whether or not there is express reference to an "implementation" or the like, various features are described, which may be variously combined and included in some implementations, but also variously omitted in other implementations. Similarly, various features are described that may be preferences or requirements for some implementations, but not other implementations.

The language used herein has been principally selected for readability and instructional purposes, and it may not have been selected to delineate or circumscribe the inventive subject matter. Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. An air cooling system for an electric vehicle charge cable, comprising:

a compressed air supply;

at least one filter;

at least one dryer;

a super cooler subsystem for chilling compressed air from the compressed air supply; and a coupling on a charging cable for supplying the chilled compressed air to the charging cable at a charging station end of the charging cable, wherein the system is configured to maintain an exterior surface of the charging cable below a predetermined temperature during vehicle charging, and wherein the compressed air is vented at a vehicle end of the charging cable opposite the charging station end or at the charging station end upon returning back from the vehicle end.

2. The air cooling system of claim 1, wherein the super cooler subsystem includes a refrigerant cycle.

3. The air cooling system of claim 2, further including a heat exchanger.

4. The air cooling system of claim 3, wherein the heat exchanger includes a refrigerant side and an air side.

5. The air cooling system of claim 4, wherein the heat exchanger is within the super cooler subsystem.

6. The air cooling system of claim 1, wherein the filter is a hydrocarbon filter.

7. The air cooling system of claim 1, wherein the dryer is a desiccant dryer.

8. The air cooling system of claim 1, wherein the vehicle end of the charging cable terminates at a connector handle configured to connect the charging cable to an electric vehicle.

9. The air cooling system of claim 8, wherein the connector handle includes a routing structure configured to redirect the chilled compressed air arriving at the connector handle back to the charging station end of the charging cable, and wherein the compressed air is vented at the charging station end upon returning back from the vehicle end.

10. An air cooled electric vehicle charging cable and system, comprising:

first and second electric vehicle charging cable portions, each portion including an insulated conductor carried in a jacket, the jacket having a wall having inner surface and defining a cooling channel extending longitudinally along the charging cable, between the jacket and the insulated conductor;

a compressed air supply;

a filter;

a dryer;

a super cooler subsystem;

a coupling on each charging cable portion for supplying chilled air to the air channels of the charging cable portions; and a connector handle, wherein the first and second charging cable portions terminate at the connector handle.

11. The air cooled electric vehicle charging cable and system of claim 10, wherein the cooling channel is series of cooling channels.

12. The air cooled electric vehicle charging cable and system of claim 11, wherein the series of cooling channels is formed by a series of inwardly extending fingers extending inwardly from the inner surface, the fingers spacing the insulator from the jacket wall, the inwardly extending fingers being spaced from one another to define air channels between the fingers that extend longitudinally along the cable.

13. The air cooled electric vehicle charging cable and system of claim 10, further including exhaust vents formed in the connector handle for discharge of the chilled air from the charging cable portions' air channels.

14. The air cooled electric vehicle charging cable and system of claim 13, wherein the exhaust vents are stationary.

15. The air cooled electric vehicle charging cable and system of claim 10, wherein the connector handle includes a routing structure configured to redirect the chilled air arriving at the connector handle back through the cable.

16. A method for air cooling an electric vehicle charging cable, the cable having first and second electric vehicle charging cable portions, each portion including an insulated conductor carried in a jacket, the jacket having a wall having inner surface and defining a cooling channel extending longitudinally along the charging cable, between the jacket and the insulated conductor, the method comprising;

compressing air to a predetermined pressure;

filtering the compressed air;

drying the compressed and filtered air;

chilling the compressed, filtered and dried air in a super cooler, the super cooler having a refrigeration cycle; and introducing the compressed, filtered, dried and chilled air into the cooling channel.

17. The method of claim 16, further including discharging the air from the cooling channel at a connector handle.

18. The method of claim 16, further including redirecting the chilled compressed air arriving at a connector handle back through the cable towards the air cooling system.

19. The method of claim 16, further including discharging the air away from the vehicle depending on ingress rating requirements of the connector handle.

* * * * *